United States Patent [19]

Samejima et al.

[11] 4,190,719

[45] Feb. 26, 1980

[54] IMIDAZOLIDONE POLYAMINES AS EPOXY CURING AGENTS

[75] Inventors: Hiroshi Samejima; Kaoru Kanayama, both of Ami, Japan

[73] Assignee: Mitsubishi Petrochemical Company Limited, Tokyo, Japan

[21] Appl. No.: 922,251

[22] Filed: Jul. 5, 1978

[30] Foreign Application Priority Data

Jul. 4, 1977 [JP] Japan .................. 52-79023

[51] Int. Cl.² .............................................. C08G 59/54
[52] U.S. Cl. ................................. 528/103; 528/111; 528/113; 528/117; 528/341; 528/367
[58] Field of Search ............... 528/117, 111, 113, 341, 528/103, 367

[56] References Cited

U.S. PATENT DOCUMENTS

| | | | |
|---|---|---|---|
| 2,847,341 | 8/1958 | Kohn | 154/140 |
| 2,994,685 | 8/1961 | Delmonte et al. | 260/47 |
| 3,530,095 | 9/1970 | Porret | 260/47 |
| 3,622,540 | 11/1971 | Hashimoto et al. | 260/47 |

Primary Examiner—Earl A. Nielsen
Attorney, Agent, or Firm—Sughrue, Rothwell, Mion, Zinn and Macpeak

[57] ABSTRACT

An epoxy resin curing agent comprising a compound represented by the formula (I):

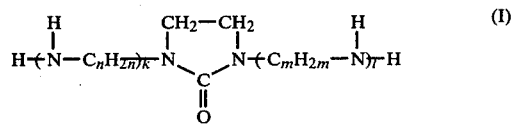

wherein k, m and n, which may be the same or different, each is an integer of 1 to 6, and l is an integer of 0 to 6, and/or a modified product thereof, a curable epoxy resin composition comprising an epoxy resin and the epoxy resin curing agent represented by the formula (I), and a cured product obtained from the epoxy resin composition.

30 Claims, No Drawings

IMIDAZOLIDONE POLYAMINES AS EPOXY CURING AGENTS

BACKGROUND OF THE INVENTION

1. Field of the Invention

This invention relates to an epoxy resin curing agent, an epoxy resin composition containing the curing agent, and a cured product of the epoxy resin composition. More particularly, the invention relates to an epoxy resin curing agent which has a low vapor pressure and has less odor and toxicity, an epoxy resin composition comprising an epoxy resin and the curing agent, and a cured product of the epoxy resin composition having high chemical resistance and improved mechanical characteristics.

2. Description of the Prior Art

Polyamines having an active hydrogen atom are utilized to a great extent in industry as a rapid curing agent for epoxy resins and providing a cured product with greatly improved physical properties as disclosed in, for example, U.S. Pat. Nos. 2,994,456 and 3,099,634. However, polyamines generally have a high vapor pressure and a strong irritating odor, and, in addition, there are various problems and health hazards such as a rash on human skin if the skin is irritated by the vapor polyamines give off. Attempts have been made to eliminate these disadvantages of polyamine curing agents by chemically modifying polyamines, for example, by reacting polyamines with epoxy group-containing compounds, acrylates, methacrylates, acrylonitrile, or aliphatic monocarboxylic acids, as disclosed in, for example, U.S. Pat. Nos. 2,890,204 and 3,205,054, but such a curing agent thus chemically modified had various defects such as an increase in the viscosity of a resin composition, which makes the curing agent difficult to handle, an impairment in the storage stability of the resin composition, or a considerable deterioration in the physical properties, such as mechanical strength and chemical resistance, of the cured product.

Another type of curing agent that has been proposed for epoxy resins to overcome the defects of polyamine curing agents is an acid anhydride curing agent as disclosed in, for example, U.S. Pat. No. 2,890,204, but as a matter of fact, an acid anhydride curing agent cannot be used as an alternative to a polyamine curing agent because a high temperature and a long time for curing are required.

U.S. Pat. No. 2,613,212 discloses 2-imidazolidones having on a ring nitrogen atom thereof an N,N'-alkylene substituent in which 2 acyclic carbon atoms separate two nitrogen atoms, with two types of such compounds being disclosed. However, there is no teaching or suggestion in U.S. Pat. No. 2,613,212 as to the ability of such compounds to cure epoxy resin compositions.

SUMMARY OF THE INVENTION

As a result of various investigations on eliminating the defects of polyamine curing agents, it has now been found that the desired purpose can be achieved by using, as a curing agent, polyamines having a specific structural formula such that a specific polyamine has been introduced into an ethylene urea skeleton.

An object of this invention is to provide an epoxy resin curing agent having a low vapor pressure and less odor and toxicity.

Another object of this invention is to provide a curable epoxy resin composition comprising an epoxy resin and an epoxy resin curing agent.

Still another object of this invention is to provide a cured product obtained from an epoxy resin composition comprising an epoxy resin and an epoxy resin curing agent.

Thus, in one embodiment, this invention provides an epoxy resin curing agent comprising a compound represented by the general formula (I):

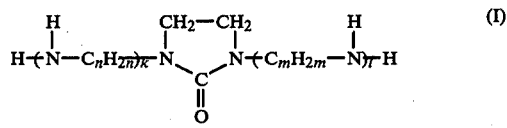

wherein k, m and n, which may be the same or different, each is an integer of 1 to 6, and l is an integer of 0 to 6, and/or a modified product thereof.

DETAILED DESCRIPTION OF THE INVENTION

A compound corresponding to the ethylene urea skeleton of the compound represented by the general formula (I) of this invention, that is, an ethylene urea compound represented by the general formula (II):

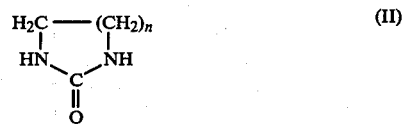

wherein n is 1 or 2, is a conventionally known epoxy resin curing agent as disclosed in, for example, German Pat. No. 1,906,515 (corresponding to Japanese Patent Publication No. 40792/70). However, this ethylene urea compound is solid at room temperature (e.g., 20°–30° C.), and has such a low compatibility and reactivity with epoxy resins that the compound requires extended heating at high temperatures (e.g., about 130°–180° C. for about 19–23 hrs.) to cure epoxy resins. Therefore, this ethylene urea compound can only be used for limited uses (e.g., baking varnishes) and is not satisfactory for practical use as a curing agent which can be employed in a wide range of applications.

On the other hand, the compound represented by the general formula (I) of this invention (hereinafter compound of this invention) is liquid at room temperature, highly compatible with epoxy resins, and easy to handle, and, therefore, epoxy resins can be easily cured even at relatively low temperatures when the compound of this invention is used as a curing agent. In addition, due to its low vapor pressure, the compound of this invention has low odor and toxicity. A further advantage of the compound of this invention is that when it is used as a curing agent for an epoxy resin composition, the physical properties, such as mechanical strength and chemical resistance, of the cured product are substantially comparable to those of the cured product obtained with an epoxy resin using an ordinary polyamine, as a curing agent. Therefore, considering all aspects together, the compound of the general formula (I) according to this invention is an excellent epoxy resin curing agent.

The compound represented by the general formula (I) of this invention can be synthesized using the following conventional methods or other suitable methods.

(i) Reaction between urea and polyalkylene polyamines (for example, as disclosed in U.S. Pat. No. 2,613,212)

(ii) Reaction between ethylene urea and polyalkylene polyamines.

Suitable polyalkylene polyamines (which also includes polyalkylene diamines) which can be reacted with urea or ethylene urea in the above synthesis methods are amines having two or more amino groups, with each amino group having at least one active hydrogen atom therein. More specifically, suitable polyalkylene polyamines which can be used are represented by the formula

wherein q is an integer of 1 to 5 and p is an integer of 2 to 6. Particularly preferred polyalkylene polyamines are diethylene triamine, triethylene tetramine, tetraethylene pentamine, pentaethylene hexamine, 1,2-diaminoethane, 1,3-diaminopropane, 1,4-diaminobutane, 1,5-diaminopentane, etc. These synthesis methods may result in the production of a mixture of two or more compounds represented by the general formula (I), and the mixture thus-obtained can, of course, be used as the curing agent of this invention with or without subsequent modification thereof.

Process (i) above can generally be conducted at a temperature of about 110° to about 200° C. and at atmospheric pressure, with a suitable molar ratio of the urea to the polyalkylene polyamine being about 0.8:1 to about 1:0.8. Process (ii) above can generally be conducted at a temperature of about 100° to about 200° C. and at atmospheric pressure, with a suitable molar ratio of the ethylene urea with the polyalkylene polyamine being about 1:1 to about 2:1. No catalysts, solvents and inert atmospheres are needed in process (i) or (ii).

Some representative examples of compounds (which includes mixtures of compounds) represented by the general formula (I) obtained by reaction of urea or ethylene urea with polyalkylene polyamines are shown by the following structural formulae:

(a) Reaction product of urea with diethylene triamine (hereafter referred to as "Compound A", for simplicity):

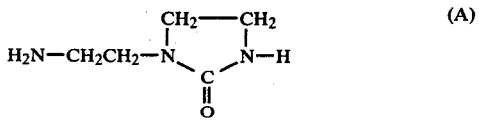

(b) Reaction product of ethylene urea with diethylene triamine (hereafter referred to as "Compound B", for simplicity):

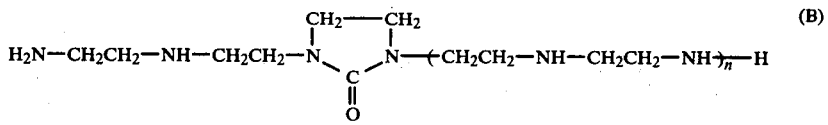

(This reaction product is normally obtained as a mixture of a compound wherein n is 0 and a compound wherein n is 1.)

(c) Reaction product of urea with tetraethylene pentamine (hereafter referred to as "Compound C", for simplicity):

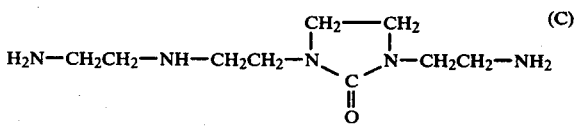

(d) Reaction product of urea with pentaethylene hexamine (hereafter referred to as "Compound D", for simplicity):

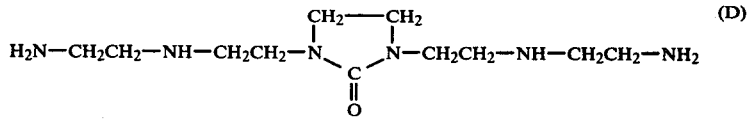

The excellent ability of the compound represented by the general formula (I) to cure an epoxy resin is not substantially reduced even if this compound is modified with an ordinary modifier in conventional methods. The modification of the compound represented by the general formula (I) can be performed using conventional techniques, e.g., heating the compound of the general formula (I) to about 50° to about 100° C. with stirring and adding a modifier over a period of about 30 to about 120 minutes. A suitable amount of the modifier which can be used to modify the compounds of the general formula (I) is a molar ratio of the modifier to the compounds of the general formula (I) of about 0.2:1 to about 1:1.

Examples of compounds which can be used in this invention to modify the compound of the general formula (I) and obtain the curing agent of this invention are epoxy group-containing compounds (such as butyl glycidyl ether, phenyl glycidyl ether, 2-ethylhexyl glycidyl ether, 2-methyloctyl glycidyl ether, lauryl glycidyl ether or diglycidyl ether of bisphenol A), acrylates (such as methyl acrylate or ethyl acrylate), methacrylates (such as methyl methacrylate or ethyl methacrylate), acrylonitrile, aliphatic monocarboxylic acids having 2 to 14 carbon atoms (such as acetic acid, butanoic acid or 2-ethylhexanoic acid), etc.

One typical example of the modified product which can be used as the curing agent according to this invention is a compound of the following formula.

(e) Modified adduct of Compound A with butyl glycidyl ether (hereafter referred to as "Compound E", for simplicity):

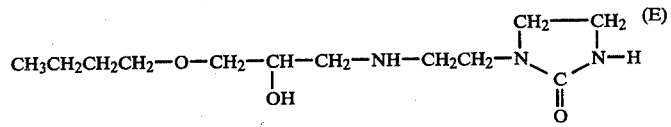

The compound of the general formula (I) and the modified product thereof may be used individually or in combination as an epoxy resin curing agent per se according to this invention. If the compound of the general formula or the modified product thereof is used individually, k+l in the general formula (I) preferably is 3 to 5. If k+l is less than 3, crystallization of the compound tends to occur. On the other hand, if k+l is larger than 5, the viscosity of the compound increases, which results in the necessity for using a diluting agent.

Example 1 of U.S. Pat. No. 2,613,212 discloses 1-$\beta$-aminoethyl-2-imidazolidone of the formula:

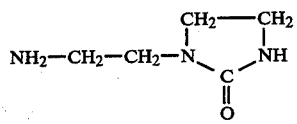

This compound corresponds to the case where k=1, l=0, m=0 and n=2 in the above-described general formula (I). The compound where k=1 and l=0 has poor liquid stability and tends to crystallize. Therefore, the compound is difficult to handle. Further, in the case of curing an epoxy resin with this compound, a brittle cured product is only obtained as compared to the use of compounds where k≧1 and l≧1. Therefore, the compound where k=1 and l=0 substantially cannot be used alone and as shown in Examples 6 and 7, described hereinafter, must be used in combination with the compounds where k≧1 and l≧1 as shown in the above-described formula (B), (C) or (D) or must be used after modifying the same with a modifier as is the above-described compound of the formula (E).

Further, two or more of the compounds of the general formula (I) and/or the modified products thereof may be used as an epoxy resin curing agent. Use of a mixture of Compound A and Compound D in a molar ratio of 1:1 to 4:1 is particularly preferred. The compound of the general formula (I) and/or the modified product thereof may also be combined or mixed with other conventional epoxy resin curing agents for use as an epoxy resin curing agent. Suitable examples of conventional epoxy resin curing agents which can be used in the present invention in combination with the compound of the general formula (I) and/or the modified product thereof are diethylene triamine, triethylene tetramine, N-aminoethylpiperazine, polyamide resins, Epomate (trademark, manufactured by Mitsubishi Petrochemical Co., Ltd.), Epicure-T (trademark, manufactured by Shell Chemical, amine value 400), etc. The conventional epoxy resin curing agent may be present in an amount of from about 10 to about 100% by weight, preferably about 30 to about 50% by weight, based on the total weight of the epoxy resin curing agent according to this invention.

The epoxy resin curing agent of this invention can be advantageously used to cure various types of epoxy resins, especially epoxy resins having two or more 1,2-epoxy groups. Suitable epoxy resins which can be used in this invention are described in various publications, such as Lee & Neville, Handbook of Epoxy Resins, McGraw-Hill Book, Co., Inc., New York (1967). Suitable epoxy resins which can be used in this invention are also commercially available under various trademarks, such as "Epikote 828" (manufactured by Shell Chemical), "Epikote 815" (manufactured by Shell Chemical), "Araldite GY260" (manufactured by Ciba Geigy), or "D.E.R. 330" (manufactured by Dow Chemical), and all of these epoxy resins can be used in this invention. The epoxy resins can be selected depending upon the intended use. Therefore, only a few representative examples of epoxy resins with which the curing agent of this invention can be applied are mentioned below, and a detailed explanation thereof is omitted.

Typical epoxy resins which can be used in this invention include glycidyl ethers of polyhydric phenols; glycidyl ethers of diphenylol alkanes, e.g., 2,2-bis(4-hydroxyphenyl)propane, 1,1-bis(4-hydroxyphenyl)ethane and bis(4-hydroxyphenyl)methane; glycidyl ethers of 4,4'-dihydroxydiphenylsulfone, hydroquinone, resorcinol, dihydroxyphenyl or dihydroxynaphthalene; glycidyl ethers of novolak or resole condensates of formaldehyde and polyhydric phenols or cresols.

Other suitable epoxy resins which can be used include poly(epoxyalkyl) ethers of aliphatic polyhydroxy compounds, e.g., epoxy compounds derived from ethylene glycol, glycerol, trimethylolpropane and pentaerythritol; polyglycidyl esters of polycarboxylic acids, e.g., phthalic acid, terephthalic acid, adipic acid, tetrahydrophthalic acid, or hexahydrophthalic acid; polyglycidyl esters of poly-unsaturated aliphatic acids, e.g., the diglycidyl ester of linolenic acid dimer; epoxidized esters of unsaturated acids, e.g., epoxidized linseed oil or soybean oil; diepoxidized butadiene, epoxidized vinylcyclohexane, 3,4-epoxycyclohexyl methyl ester of 3,4-epoxycyclohexane carboxylic acid; polyglycidyl isocyanurate; diglycidylaniline; copolymers of styrene and glycidyl methacrylate; copolymers of acrylonitrile and glycidyl methacrylate; copolymers of styrene and arylglycidyl ethers; or mixtures thereof.

A suitable range for the epoxy equivalent of these epoxy resins is about 100 to about 3,000, preferably about 140 to about 300.

The most suitable examples of epoxy resins which can be used in this invention are a diepoxy ether of a bisphenol (such as a diglycidyl ether of bisphenol A), a diepoxy ester of a dicarboxylic acid (such as a diglycidyl ester of hexahydrophthalic acid), a diepoxy derivative of a diene (such as vinyl cyclohexene dioxide), and the like.

The epoxy resin curing agent of this invention is generally used in an amount of from about 20 to about 60 equivalents per epoxy equivalent of the epoxy resin, but this amount can be appropriately changed as needed. The epoxy resin curing agent of this invention is preferably used in an equivalent amount per epoxy equivalent of the epoxy resin.

A curable epoxy resin composition comprising an epoxy resin and the epoxy resin curing agent of this invention can generally be cured at a temperature in the range of about 0° to about 200° C. Especially, the epoxy resin curing agent of this invention can be used as a satisfactory substitute for a polyamine curing agent because such can be cured even at relatively low temperatures such as room temperature (e.g., 20°–30° C.). The time required for curing varies depending upon the curing temperature and the like, but normally, the curing time can be appropriately selected within a range of about 10 minutes to about 20 hours, preferably about 20 to about 30 minutes.

As in the case with conventional curing agents, a curable epoxy resin composition containing the curing agent of this invention can be compounded with an extender, a filler, a reinforcing agent, a fire retardant and a pigment (or a dye) at various stages prior to curing. Examples of suitable extenders which can be used include pulverized stone, sand, silica, talc, calcium carbonate and the like, e.g., in an amount of about 100 to about 200 parts by weight per 100 parts by weight of the epoxy resin. Examples of suitable fillers include aluminum oxide, barium titanate, quartz powder, a ceramic powder and the like, e.g., in an amount of about 300 to about 900 parts by weight per 100 parts by weight of the epoxy resin. Examples of suitable reinforcing agents include mica, asbestos and the like, e.g., in an amount of about 5 to about 10 parts by weight per 100 parts by weight of the epoxy resin. Examples of suitable fire retardants include antimony oxide and the like, e.g., in an amount of about 100 to about 200 parts by weight per 100 parts by weight of the epoxy resin. Examples of suitable pigments (or dyes) include titanium dioxide, Cadmium Red Medium (trademark, produced by Chemical and Pigment Co.), Cadmalith Golden (trademark, produced by Chemical and Pigment Co.), National Fast Red (trademark, produced by American Cyanamid Co.), Calco Condensation (trademark, produced by American Cyanamid Co.), Green AY (trademark, produced by American Cyanamid Co.) and the like, e.g., in an amount of about 30 to about 60 parts by weight per 100 parts by weight of the epoxy resin. The curable epoxy resin composition having the curing agent of this invention incorporated therein can be extensively used as a variety of molded articles, cast articles, impregnating materials, paints and adhesives.

This invention is illustrated in greater detail by reference to the following examples and comparative curing evaluations. Unless otherwise indicated, all parts and percents are by weight.

EXAMPLES 1 TO 4

A 200 ml glass flask equipped with a thermometer, a stirrer, a fractionating column and a gas inlet was charged with the ureas, the polyamines and distilled water in the amounts shown in Table 1 below, and the mixture was heated to 100° to 160° C. While removing gaseous ammonia and water generated as the reaction proceeded, the reaction was continued for about 3 to 10 hours until no more gaseous ammonia and water were generated.

After completion of the reaction, the residual gas and the unreacted materials were removed at a reduced pressure of 0.5 to 1 mmHg with stirring for about 1 hour to obtain the curing agents as shown in Table 1 below (Compounds A to D).

EXAMPLE 5

A flask equipped with a stirrer, a dropping funnel and a thermometer was charged with 25.8 g of Compound A prepared in Example 1. While the contents were being heated at 60° C., 8.6 g of butyl glycidyl ether was added dropwise thereto over a period of 10 minutes. After stirring for about 2 hours additionally after the dropwise addition, a modified curing agent as shown in Table 1 below (Compound E) was produced.

Table 1 below shows the starting materials, the amount of these materials charged, and the yield, appearance and odor of the compound produced in each Example.

Table 1

| Example (name of compound) | Materials and Amounts Charged | | | Compound, Yield, Appearance and Odor | | |
|---|---|---|---|---|---|---|
| | Urea (g) | Polyamine (g) | Water (g) | Compound Produced (g) | Appearance | Odor |
| Example 1 (Compound A) | Urea (18.2) | DETA[1] (30.9) | (18) | A (46.2) | Pale yellow, transparent liquid | Negligible |
| Example 2 (Compound B) | Ethylene urea (8.6) | DETA (51.6) | — | B[4] (16.9) | Pale yellow, transparent liquid | " |
| Example 3 (Compound C) | Urea (36.4) | TEPA[2] (113.6) | (46) | C (185.7) | Pale yellow, transparent liquid | " |
| Example 4 (Compound D) | Urea (232.2) | PEHA[3] (60.1) | (70) | D (290.4) | Reddish brown, transparent liquid | " |
| Example 5 (Compound E) | Compound A (25.8) | Butyl glycidyl ether (8.6) | | E (34.0) | Pale yellow, transparent liquid | " |

Notes:
[1] Diethylene triamine
[2] Tetraethylene pentamine
[3] Pentaethylene hexamine
[4] A mixture of about 75% by weight of Compound B wherein n is 1 and about 25% by weight of Compound B wherein n is 0.

Vapor Pressure and Odor Measurement

The vapor pressure and the odor of each of the curing agents prepared in Example 3 (Compound C), Example 4 (Compound D), and Example 5 (Compound E), as well as those of conventional curing agents were measured.

The results obtained are shown in Table 2 below.

Table 2

| Compound | Vapor Pressure (mm Hg) | | Odor Rating[1] | |
|---|---|---|---|---|
| | 20° C. | 50° C. | 20° C. | 80° C. |
| Curing Agents of the Invention | | | | |
| Compound C | $2.5 \times 10^{-7}$ | $1.4 \times 10^{-6}$ | o | o |
| Compound D | $1.8 \times 10^{-8}$ | $3.1 \times 10^{-7}$ | o | Δ |
| Compound E | $5.1 \times 10^{-6}$ | $9.1 \times 10^{-4}$ | o | o |
| Conventional Curing Agents | | | | |
| TEPA[2] | $3.6 \times 10^{-5}$ | $2.0 \times 10^{-4}$ | Δ | x |
| TETA[3] | $4.7 \times 10^{-2}$ | $8.3 \times 10^{-2}$ | Δ | x |
| DETA[4] | $2.2 \times 10^{-1}$ | 1.4 | Δ | Δ |
| Xylenediamine | $2.9 \times 10^{-3}$ | $4.1 \times 10^{-2}$ | Δ | x |
| Polyamide[5] | $1.3 \times 10^{-7}$ | $1.6 \times 10^{-5}$ | x | x |
| Aminoethyl-piperazine | $3.9 \times 10^{-2}$ | $5.6 \times 10^{-1}$ | x | x |

Notes:
[1] The following method was used for measurement of odor. 2 cc of a sample was placed in a 100 cc sampling tube provided with a screw cap, and (1) allowed to stand for a day at room temperature (20° C.) or (2) heated at 80° C. for 1 hour. The following odor ratings were used:
Negligible Odor o
Bearable Odor Δ
Unbearable Odor x
[2] Tetraethylene pentamine
[3] Triethylene tetramine
[4] Diethylene triamine
[5] Amine Value 400

As the results in Table 2 clearly show, each curing agent of this invention had a much lower vapor pressure than the vapor pressure of conventional curing agents, and the odor of the curing agents of this invention was negligible as compared with that of the conventional curing agents.

Skin Irritation Test

Compound C obtained in Example 3 and a conventional curing agent, triethylene tetramine (TETA), were subjected to skin irritation testing. The details of the test were as follows.

Animal: Japanese white male rabbits of the native kind

Application: A coating of 0.25 ml of the sample was applied to a circular site (3 cm in diameter) on the dorsal skin (sheared with clippers and depilated with a depilatory cream). After fixing the sample with gauze and adhesive tape, a moisture-proof rubber covering was applied to the site, which was then bound with an elastic bandage. After standing for 4 hours, the site was cleaned.

Observation: 4, 24, 48 and 72 hours after application.
Ratings:
(a) Formation of Erythema and Scab
No change 0
Slight erythema 1
Erythema (part of the site) 2
Erythema (most of the site) 3
Erythema (all of the site) 4
(b) Formation of Edema
No change 0
Slight edema 1
Edema (part of the site) 2
Edema (most of the site) 3
Edema (all of the site) 4

Table 3

| Sample | Rabbit No. | Erythema Scab | | | | Edema | | | | Mean Value | Primary Irritation Score |
|---|---|---|---|---|---|---|---|---|---|---|---|
| | | 4 hr | 24 hr | 48 hr | 72 hr | 4 hr | 24 hr | 48 hr | 72 hr | | |
| Compound C | 1 | 1 | 0 | 0 | 0 | 0 | 0 | 0 | 0 | 0.25 | |
| | 2 | 0 | 1 | 1 | 1 | 0 | 1 | 1 | 1 | 1.5 | 0.83 |
| | 3 | 0 | 1 | 1 | 1 | 0 | 0 | 0 | 0 | 0.75 | |
| TETA | 4 | 2 | 2 | 2 | 2 | 2 | 2 | 2 | 2 | 4 | |
| | 5 | 2 | 3 | 3 | 3 | 3 | 2 | 2 | 2 | 5 | 4.25 |
| | 6 | 2 | 2 | 2 | 2 | 2 | 2 | 2 | 1 | 3.75 | |

Notes:
1. Test using healthy skin
2. The following evaluation was obtained in terms of primary irritation scores.
Score of 2 or less: slight irritation
Score of 2 to 5: fair irritation
Score of 5 or more: strong irritation As the results in Table 3 clearly show, Compound C of this invention had an extremely low irritative effect on the skin.

Curing Evaluation 1

Five curable epoxy resin formulations were prepared by compounding an epoxy resin, Epikote #828 (trademark for a diglycidyl ether of bisphenol A manufactured by Shell Chemical, epoxy equivalent 190), with Compounds B, C, D, E of this invention and a conventional diethylene triamine curing agent in the proportions as shown in Table 4 below. Each formulation was cast into a casting mold and heated at 80° C. for 3 hours to cure.

The physical properties of each of the cured products obtained are shown in Table 4 below.

The following method was used to determine the physical properties.

| Heat Distortion Temperature: | ASTM D-648 |
|---|---|
| Impact Test: | ASTM D-256 (the notch in a test piece was 0.07 cm deep) |
| Flexural Test: | JIS K-6911 |
| Chemical Resistance: | JIS K-6911 |

Table 4

| | Run No. | | | | |
|---|---|---|---|---|---|
| | 1 | 2 | 3 | 4 | 5(control) |
| Proportions (parts) | | | | | |
| Epoxy Resin | | | | | |
| Epikote #828 | 100 | 100 | 100 | 100 | 100 |
| Curing Agent | | | | | |
| Diethylene Triamine | — | — | — | — | 8 |
| Compound B | — | — | — | 20 | — |
| Compound C | 30 | — | — | — | — |
| Compound D | — | 30 | — | — | — |
| Compound E | — | — | 50 | — | — |
| Properties | | | | | |
| Heat Distortion Temperature (°C.) | 79 | 90 | 68 | 83 | 92 |
| Izod Impact Strength (kg . cm/cm$^2$) | 5.8 | Not measured | Not measured | Not measured | 2.9 |
| Flexural Strength (kg/mm$^2$) | 14.9 | 15.5 | 12.5 | 14.0 | 14.5 |
| Flexural Modulus (kg/mm$^2$) | 339 | 510 | 260 | 340 | 551 |
| Maximum Strain (mm) | 9.3 | 5.2 | 13 | 8.0 | 9.1 |
| Chemical Resistance (% wt. increase) | | | | | |
| H$_2$O | +0.4 | +0.3 | — | +0.3 | +0.3 |
| 5% NaOH | +0.4 | +0.4 | — | +0.4 | +0.5 |
| 5% HCl | +1.0 | +0.9 | — | +0.9 | +1.4 |
| Toluene | +0.2 | +0.2 | — | +0.1 | +0.5 |
| Methyl Ethyl Ketone | +0.1 | +0.1 | +0.2 | +0.1 | +5.2 |
| Methanol | +5.2 | +3.5 | — | +4.0 | +3.4 |

As is clear from the results in Table 4 above, the epoxy resin curing agents of this invention (Compounds B to E) provided a cured product having a higher chemical resistance than and substantially equal mechanical characteristic as compared with the cured product obtained using diethylene triamine curing agent. The fact that the epoxy resin curing agents of this invention, which are substantially free from odor and toxicity problems, provide a cured product exhibiting physical properties no less inferior to those of the cured products obtained using the diethylene triamine curing agent which is extremely malodorous and highly toxic, demonstrates that, considering all aspects together, the epoxy resin curing agent of this invention is far superior to conventional epoxy resin curing agents.

Curing Evaluation 2

A formulation was prepared by compounding 100 parts of Chisso Nox #221 (trademark for an alicyclic epoxy resin, manufactured by Chisso Corporation, epoxy equivalent 140) with 23 parts of Compound C.

The formulation was heated at 80° C. for 3 hours, then at 120° C. for 4 hours, to obtain a transparent rigid cured product.

Curing Evaluation 3

Epikote #828 (trademark for an epoxy resin, manufactured by Shell Chemical, epoxy equivalent 190) was cured using each of the curing agent prepared in Example 3 (Compound C), a commercial curing agent "Epomate B-002" (trademark for an epoxy resin curing agent, manufactured by Mitsubishi Petrochemical Co., Ltd.), a mixture of Compound C and Epomate B-002 (1:1 by weight ratio) and tetraethylene pentamine (TEPA). The physical properties of each of the cured products obtained were tested.

The curing conditions and the physical properties of each of the cured products obtained are set forth in Table 5 below.

Table 5

| Formulation (parts) | | Conditions | Heat Distortion Temperature (°C.) | Bending Test | | | Izod Impact Strength (kg . cm/cm$^2$) | Chemical Resistance[1] | | | | | |
|---|---|---|---|---|---|---|---|---|---|---|---|---|---|
| | | | | Strength (kg/mm$^2$) | Modulus (kg/mm$^2$) | Max. Strain (mm) | | H$_2$O | 5% HCL | 5% NaOH | Methanol | Toluene | Methyl Ethyl Ketone |
| Resin | 100 | 80° C. × 3 hr | 79 | 14.9 | 339 | 7.2 | 5.8 | 0.4 | 1.0 | 0.4 | 5.2 | 0.2 | 0.1 |
| Compound C | 30 | | | | | | | | | | | | |
| Resin | 100 | 80° C. × 3 hr | 81 | 13 | 478 | 13.2 | 13.2 | 1.0 | 2.7 | 1.0 | 11.0 | 6.2 | 0.3 |
| Compound C | 20 | | | | | | | | | | | | |
| Epomate B-002 | | | | | | | | | | | | | |
| Resin | 100 | 80° C. × 3 hr | 78 | 11.2 | 256 | Not broken | 8.9 | 1.2 | 1.5 | 1.2 | 11.6 | 0.4 | 20 |
| Epomate B-002 | 50 | | | | | | | | | | | | |
| Resin | 100 | 80° C. × 3 hr | 109 | 12.2 | 371 | 9 | — | 0.5 | 0.8 | 0.5 | 3.7 | — | 0 |
| TEPA | 20 | | | | | | | | | | | | |

[1]The weight increase (in %) after immersion in each chemical for 7 days.

The results in Table 5 show that the epoxy resin curing agent prepared according to this invention is a good curing agent because it compares favorably with or even excels the commercially available epoxy resin curing agent Epomate B-002, and that it is not much inferior to TEPA, which is highly odorous and toxic, as an epoxy resin curing agent.

EXAMPLE 6

A reaction vessel equipped with a water separator was charged with 36.4 g of diethylene triamine, 40.0 g of tetraethylene pentamine, 33.9 g of urea and 9.0 g of water, and the mixture was heated at 160° C. with stirring. Water was distilled off during the course of a vigorous deammonation reaction which continued for 3 hours. Thereafter, using a water aspirator, the reaction vessel was placed under a reduced pressure of 30 to 50 mm Hg for a 30 minute period to remove the residual ammonia. A pale yellow transparent compound substantially free from any odor was obtained in an amount of 91.1 g. This compound had a viscosity of 59 poise (at 25° C.), had an amine value of 430 KOH mg/g and contained 0% diethylene triamine and 3.5% tetraethylene pentamine, as unreacted amines.

A formulation of 100 parts of Epikote #828 and 35 parts of the compound produced as described above was allowed to stand at 25° C. for 1 week to obtain a strong, cured product which had a heat distortion temperature of 76° C.

EXAMPLE 7

A reaction vessel was charged with 36.4 g of diethylene triamine, 40.0 g of tetraethylene pentamine and 33.9 g of urea, and heated at 200° C. with stirring. After completion of the reaction, using a water aspirator, the reaction vessel was placed under a reduced pressure of 30 to 50 mm Hg for 30 minutes to remove the residual ammonia. A pale yellow transparent compound substantially free from any odor was obtained. The compound had the following characteristics.

Amine Value: 485 KOH mg/g
Viscosity: 22 poise (at 25° C.)
Unreacted Amines: 0.1% or less of diethylene triamine and 4.4% of tetraethylene pentamine
Hue (Gardner color number): 2 to 3

A formulation of 100 parts of Epikote #828 and 35 parts of the compound produced above was heated at 80° C. for 3 hours to obtain a strong, cured product, which had a heat distortion temperature of 82° C., a bending strain of 13.2 mm, a flexural strength of 14.9 kg/mm² and a flexural modulus of 552 kg/mm².

While the invention has been described in detail and with reference to specific embodiments thereof, it will be apparent to one skilled in the art that various changes and modifications can be made therein without departing from the spirit and scope thereof.

What is claimed is:

1. A curable epoxy resin composition comprising (a) an epoxy resin and (b) an epoxy resin curing agent, wherein the epoxy resin curing agent is an epoxy resin curing agent represented by the formula (I):

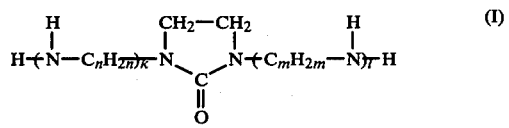

wherein k, m and n, which may be the same or different, each is an integer of 1 to 6, and l is an integer of 0 to 6, and/or a modified product thereof.

2. The curable epoxy resin composition of claim 1, wherein said epoxy resin (a) is selected from the group consisting of a diglycidyl ether of a bisphenol, a diglycidyl ester of a dicarboxylic acid and a diepoxy derivative of a diene.

3. The curable epoxy resin composition of claim 2, wherein said epoxy resin is a diglycidyl ether of a bisphenol.

4. The curable epoxy resin composition of claim 1, wherein the amount of said epoxy resin curing agent (b) is from about 20 to about 60 equivalents per epoxy equivalent of the epoxy resin (a).

5. The curable epoxy resin composition of claim 1, wherein said compound represented by the general formula (I) is a reaction product of a polyalkylene polyamine with urea or ethylene urea.

6. The curable epoxy resin composition of claim 5, wherein said polyalkylene polyamine is an amine having two or more amino groups, with each amino group having at least one active hydrogen atom.

7. The curable epoxy resin composition of claim 5, wherein said polyalkylene polyamine is at least one member selected from the group consisting of diethylene triamine, triethylene tetramine, tetraethylene pentamine, pentaethylene hexamine, 1,2-diaminoethane, 1,3-diaminopropane, 1,4-diaminobutane and 1,5-diaminopentane.

8. The curable epoxy resin composition of claim 1, wherein said compound represented by the general formula (I) is at least one member selected from the group consisting of a reaction product of urea with diethylene triamine, a reaction product of ethylene urea with diethylene triamine, a reaction product of urea with tetraethylene pentamine and a reaction product of urea with pentaethylene hexamine.

9. The curable epoxy resin composition of claim 8, wherein said compound represented by the general formula (I) is a mixture of a reaction product of urea with diethylene triamine and a reaction product of urea with pentaethylene hexamine.

10. The curable epoxy resin composition of claim 9, wherein the molar ratio of said reaction product of urea with diethylene triamine to said reaction product of urea with pentaethylene hexamine is 1:1 to 4:1.

11. The curable epoxy resin composition of claim 1, wherein k is an integer of 1 to 4 and l is 0.

12. The curable epoxy resin composition of claim 1, wherein k+l is an integer of 3 to 5.

13. The curable epoxy resin composition of claim 1, wherein said modified product of the compound represented by the general formula (I) is obtained by modifying the compound of the general formula (I) with a compound selected from the group consisting of an epoxy group-containing compound, an acrylate, a methacrylate, acrylonitrile and an aliphatic monocarboxylic acid having 2 to 14 carbon atoms.

14. The curable epoxy resin composition of claim 13, wherein said epoxy group-containing compound is butyl glycidyl ether.

15. A cured epoxy resin product comprising the product obtained on curing a curable epoxy resin composition comprising (a) an epoxy resin and (b) an epoxy resin curing agent, wherein the epoxy resin curing agent is an epoxy resin curing agent represented by the formula (I):

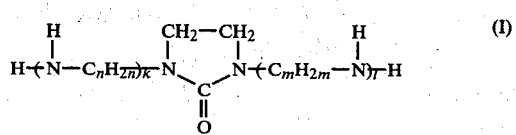

wherein k, m and n, which may be the same or different, each is an integer of 1 to 6, and l is an integer of 0 to 6, and/or a modified product thereof.

16. The cured epoxy resin product of claim 26, wherein the curing is conducted at about 0° to about 200° C. for about 10 minutes to about 20 hours.

17. In a method for curing an epoxy resin comprising incorporating an epoxy resin curing agent into an epoxy resin and heating the combination of the epoxy resin and the epoxy resin curing agent, the improvement which comrpises said epoxy resin curing agent being represented by the formula (I):

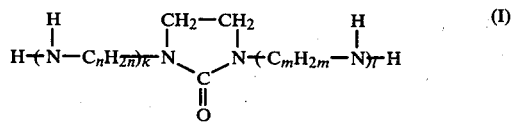

wherein k, m and n, which may be the same or different, each is an integer of 1 to 6, and l is an integer of 0 to 6, and/or a modified product thereof.

18. The method of curing an epoxy resin of claim 17, wherein said epoxy resin is selected from the group consisting of a diglycidyl ether of a bisphenol, a diglycidyl ester of a dicarboxylic acid and a diepoxy derivative of a diene.

19. The method of curing an epoxy resin of claim 18, wherein said epoxy resin is a diglycidyl ether of a bisphenol.

20. The method of curing an epoxy resin of claim 18, wherein the amount of said epoxy resin curing agent is from about 20 to about 60 equivalents per epoxy equivalent of the epoxy resin.

21. The method of curing an epoxy resin of claim 18, wherein said compound represented by the general formula (I) is a reaction product of a polyalkylene polyamine with urea or ethylene urea.

22. The method of curing an epoxy resin of claim 21, wherein said polyalkylene polyamine is an amine having two or more amino groups, with each amino group having at least one active hydrogen atom.

23. The method of curing an epoxy resin of claim 21, wherein said polyalkylene polyamine is at least one member selected from the group consisting of diethylene triamine, triethylene tetramine, tetraethylene pentamine, pentaethylene hexamine, 1,2-diaminoethane, 1,3-diaminopropane, 1,4-diaminobutane and 1,5-diaminopentane.

24. The method of curing an epoxy resin of claim 17, wherein said compound represented by the general formula (I) is at least one member selected from the group consisting of a reaction product of urea with diethylene triamine, a reaction product of ethylene urea with diethylene triamine, a reaction product of urea with tetraethylene pentamine and a reaction product of urea with pentaethylene hexamine.

25. The method of curing an epoxy resin of claim 24, wherein said compound represented by the general formula (I) is a mixture of a reaction product of urea with diethylene triamine and a reaction product of urea with pentaethylene hexamine.

26. The method of curing an epoxy resin of claim 25, wherein the molar ratio of said reaction product of urea with diethylene triamine to said reaction product of urea with pentaethylene hexamine is 1:1 to 4:1.

27. The method of curing an epoxy resin of claim 17, wherein k is an integer of 1 to 4 and l is 0.

28. The method of curing an epoxy resin of claim 17, wherein k+l is an integer of 3 to 5.

29. The method of curing an epoxy resin of claim 17, wherein said modified product of the compound represented by the general formula (I) is obtained by modifying the compound of the general formula (I) with a compound selected from the group consisting of an epoxy group-containing compound, an acrylate, a methacrylate, acrylonitrile and an aliphatic monocarboxylic acid having 2 to 14 carbon atoms.

30. The method of curing an epoxy resin of claim 29, wherein said epoxy group-containing compound is butyl glycidyl ether.

* * * * *